(12) United States Patent
Sawada et al.

(10) Patent No.: US 8,653,463 B2
(45) Date of Patent: Feb. 18, 2014

(54) RADIATION DETECTION APPARATUS AND RADIATION IMAGING SYSTEM

(75) Inventors: Satoru Sawada, Kodama-gun (JP); Masato Inoue, Kumagaya (JP); Noriaki Oguri, Zama (JP); Shinichi Takeda, Honjo (JP); Masayoshi Akiyama, Yokohama (JP); Taiki Takei, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 226 days.

(21) Appl. No.: 13/110,132

(22) Filed: May 18, 2011

(65) Prior Publication Data
US 2011/0315886 A1    Dec. 29, 2011

(30) Foreign Application Priority Data

Jun. 24, 2010   (JP) .................................. 2010-143919
Nov. 15, 2010   (JP) .................................. 2010-255311

(51) Int. Cl.
*G01T 1/20*    (2006.01)
*H01L 27/00*   (2006.01)

(52) U.S. Cl.
USPC .................................... 250/361 R; 250/208.1

(58) Field of Classification Search
USPC ................... 250/366, 361 R, 338.4; 257/428, 257/E31.129
See application file for complete search history.

(56) References Cited

U.S. PATENT DOCUMENTS

| | | | |
|---|---|---|---|
| 6,025,598 A | 2/2000 | Tago | 250/370.01 |
| 7,256,404 B2 | 8/2007 | Inoue et al. | 250/370.11 |
| 7,391,029 B2 | 6/2008 | Takeda et al. | 250/370.11 |
| 7,435,968 B2 * | 10/2008 | Watanabe et al. | 250/370.14 |
| 7,514,686 B2 | 4/2009 | Ogawa et al. | 250/361 |
| 7,550,055 B2 * | 6/2009 | Le et al. | 156/276 |
| 7,572,659 B2 * | 8/2009 | Tsubaki et al. | 438/48 |
| 7,595,493 B2 | 9/2009 | Okada et al. | 250/370.11 |
| 7,692,152 B2 | 4/2010 | Inoue | 250/361 |
| 7,714,294 B2 | 5/2010 | Sawada et al. | 250/370.11 |
| 7,723,693 B2 | 5/2010 | Okada et al. | 250/370.01 |

(Continued)

FOREIGN PATENT DOCUMENTS

| | | |
|---|---|---|
| CN | 1873049 | 12/2006 |
| CN | 1925162 | 3/2007 |
| JP | 2008-224429 | 9/2008 |

OTHER PUBLICATIONS

Office Action issued May 13, 2013 in counterpart Chinese Patent Application No. 201110166963.5, with translation.

*Primary Examiner* — David Porta
*Assistant Examiner* — Abra Fein
(74) *Attorney, Agent, or Firm* — Fitzpatrick, Cella, Harper & Scinto

(57) ABSTRACT

A radiation detection apparatus comprising semiconductor substrates each having a first surface on which a photoelectric conversion portion is formed and a second surface opposite to the first surface; a scintillator layer, placed over the first surfaces of the semiconductor substrates, for converting radiation into light; and an elastic member, placed between a base and the second surfaces, for supporting the second surfaces of the semiconductor substrates such that the first surfaces of the semiconductor substrates are flush with each other is provided. In measurement of the elastic member as a single body, an amount of stretch of a cubic specimen in a direction parallel to the first surface when being compressed in a direction perpendicular to the first surface is smaller than an amount of stretch of the specimen in the direction perpendicular to the first surface when being compressed in the direction parallel to the first surface.

9 Claims, 5 Drawing Sheets

(56) References Cited

U.S. PATENT DOCUMENTS

| | | |
|---|---|---|
| 7,777,167 B2 | 8/2010 | Takeda et al. .................. 250/205 |
| 7,952,058 B2 | 5/2011 | Nomura et al. ............. 250/208.1 |
| 2007/0132045 A1 | 6/2007 | Tsubaki et al. ................ 257/414 |
| 2007/0272870 A1* | 11/2007 | Ishii et al. ................ 250/370.08 |
| 2009/0230171 A1* | 9/2009 | Matsumura et al. ......... 228/44.7 |
| 2009/0283685 A1 | 11/2009 | Takeda et al. ............ 250/370.11 |
| 2009/0317633 A2* | 12/2009 | Yamamoto .................... 428/343 |
| 2010/0102236 A1 | 4/2010 | Inoue et al. ................... 250/361 |

* cited by examiner

RADIATION DETECTION APPARATUS AND RADIATION IMAGING SYSTEM

BACKGROUND OF THE INVENTION

1. Field of the Invention

The present invention relates to a radiation detection apparatus and a radiation imaging system. In this specification, radiation includes electromagnetic waves such as X-rays and γ-rays.

2. Description of the Related Art

Recently implemented semiconductor substrates of radiation detection apparatuses have large areas. The larger the area of the semiconductor substrate, the lower the yield per unit of substrate, and the greater the amount of loss per unit of substrate. For this reason, a plurality of semiconductor substrates is arrayed to achieve increases in the areas of the semiconductor substrates. When arraying a plurality of semiconductor substrates, it is preferable that they have a uniform height. According to Japanese Patent Laid-Open No. 2008-224429, the height of the upper surface of a semiconductor substrate is adjusted by bonding the lower surface of the semiconductor substrate to a base through a sheet-like porous damper member.

SUMMARY OF THE INVENTION

When arraying a plurality of semiconductor substrates, it is necessary to set proper intervals between the semiconductor substrates as well as making their upper surfaces have a uniform height. The technique disclosed in Japanese Patent Laid-Open No. 2008-224429 can equalize the surface heights of semiconductor substrates by making a damper member contract in a direction perpendicular to the upper surface of each semiconductor substrate. At the same time, however, because the damper member stretches in a direction parallel to each semiconductor substrate, the intervals between the semiconductor substrates increase. One aspect of the present invention therefore provides a technique of suppressing shifts in the intervals between a plurality of semiconductor substrates in a radiation detection apparatus in which the semiconductor substrates are arranged.

An aspect of the present invention provides a radiation detection apparatus comprising: a plurality of semiconductor substrates each having a first surface on which a photoelectric conversion portion for detecting light is formed and a second surface opposite to the first surface; a scintillator layer, placed over the first surfaces of the plurality of semiconductor substrates, for converting radiation into light; and an elastic member, placed between a base and the second surfaces of the plurality of semiconductor substrates, for supporting the second surfaces of the plurality of semiconductor substrates such that the first surfaces of the plurality of semiconductor substrates are flush with each other, wherein, in measurement of the elastic member as a single body, an amount of stretch of a cubic specimen in a direction parallel to the first surface when being compressed in a direction perpendicular to the first surface is smaller than an amount of stretch of the specimen in the direction perpendicular to the first surface when being compressed in the direction parallel to the first surface.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

The embodiments of the present invention will be described below with reference to the accompanying drawings.

Figure 1:
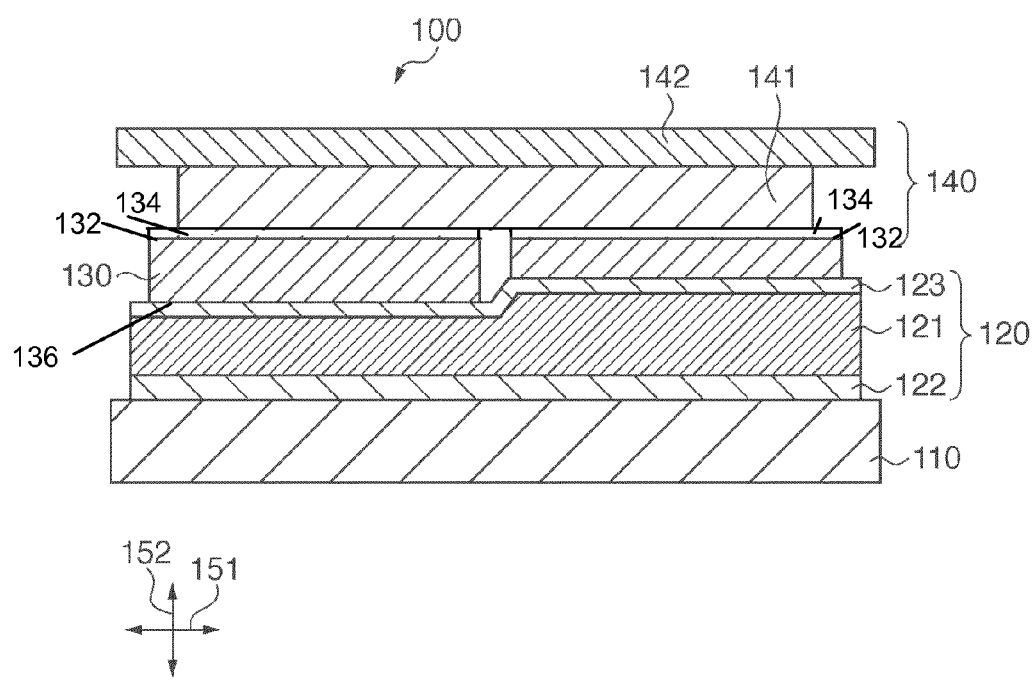
FIG. 1 is a schematic sectional view of an example of a radiation detection apparatus according to one embodiment.

An example of a radiation detection apparatus 100 according to one embodiment will be described with reference to FIG. 1. FIG. 1 is a schematic sectional view of the radiation detection apparatus 100. The radiation detection apparatus 100 may include a base 110, an elastic member 120, a plurality of semiconductor substrates 130, and a scintillator panel 140. The scintillator panel 140 may include a scintillator layer 141 and a support substrate 142. The scintillator layer 141 converts radiation which has entered the radiation detection apparatus 100 into light. The scintillator layer 141 may be formed by, for example, vapor-depositing CsI on the support substrate 142.

The semiconductor substrate 130 has a surface (first surface) 132 on which a photoelectric conversion portion 134 is formed, and detects light converted by the scintillator layer 141. The scintillator panel 140 is placed over the surface (first surface) 132 on which the photoelectric conversion portion 134 is formed. The radiation detection apparatus 100 may include a plurality of semiconductor substrates 130. FIG. 1 shows the two semiconductor substrates 130 as an example. However, the number of substrates that may be used is not limited to this. The surfaces of the semiconductor substrates 130 which are located on the scintillator panel 140 side are fixed to be flush with each other. The surfaces (second surfaces) 136 of the semiconductor substrates 130 which are located on the side opposite to the scintillator panel 140 are supported by the elastic member 120 fixed to the base 110.

The elastic member 120 may include a base material 121 and adhesion layers 122 and 123 sandwiching the base material 121. The semiconductor substrates 130 are bonded to the base material 121 through the adhesion layer 123. The base 110 is bonded to the base material 121 through the adhesion layer 122. That is, the elastic member 120 also serves as an adhesion member. The base material 121 may be covered by an adhesive material instead of being sandwiched between the adhesion layers 122 and 123.

Figure 2:
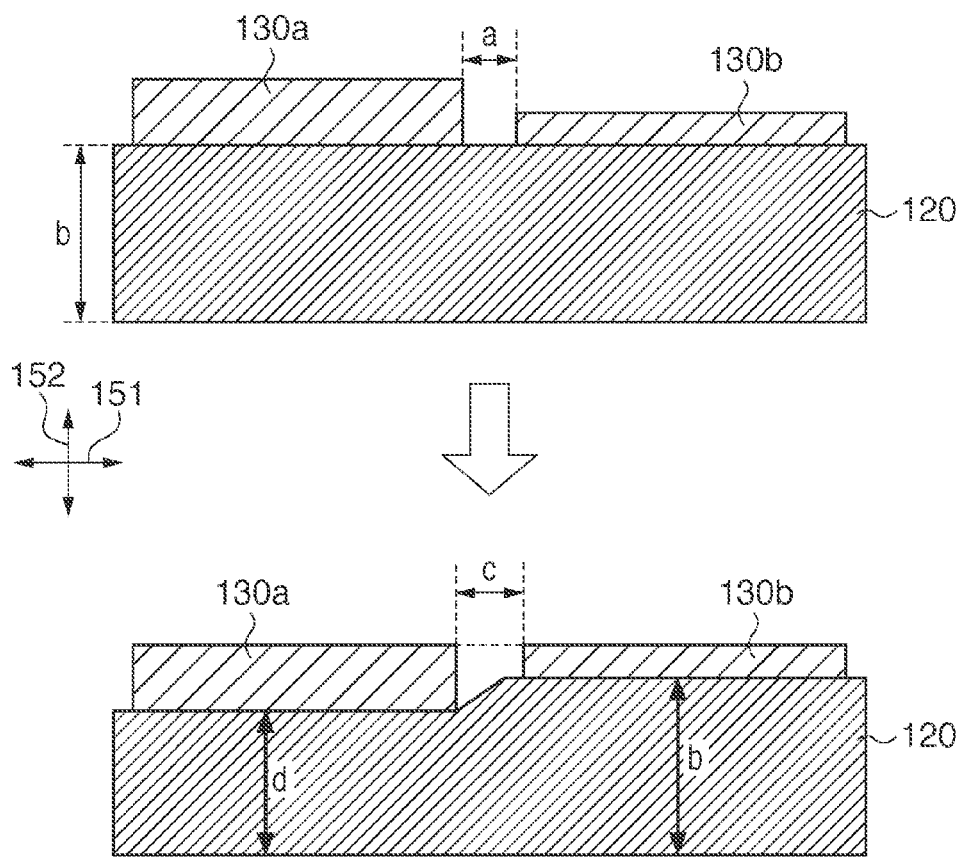
FIG. 2 is a view for explaining the anisotropy of a base material.

For the sake of the following description, a direction parallel to the surface of the semiconductor substrate 130 which is located on the scintillator panel 140 side will be simply referred to as a parallel direction 151, and a direction perpendicular to the surface will be simply referred to as a perpendicular direction 152. The base material 121 has anisotropy with respect to the amount of stretch. Assume that a cubic specimen is extracted from the base material 121 and is singly measured. The amount of stretch of this specimen in the parallel direction 151 upon compression in the perpendicular direction 152 is smaller than that in the perpendicular direction 152 upon compression in the parallel direction 151. This will be described in detail with reference to FIG. 2. The upper portion of FIG. 2 shows a state in which a semiconductor substrate 130a and a semiconductor substrate 130b are aligned on the elastic member 120. Assume that in this case, the thickness (the length in the perpendicular direction 152) of the semiconductor substrate 130a is larger than the thickness of the semiconductor substrate 130b. The interval between the semiconductor substrate 130a and the semiconductor substrate 130b is represented by a, and the length of the elastic member 120 in the perpendicular direction 152 is represented by b. In this state, the semiconductor substrate 130a is pressed into the elastic member 120 such that the surfaces of the semiconductor substrates 130a and 130b which are located on the scintillator panel 140 side are flush with each other. As a result, as indicated by the lower portion of FIG. 2, the interval between the semiconductor substrate 130a and the semiconductor substrate 130b becomes an interval c, and the length of a portion of the elastic member 120 which is located under the semiconductor substrate 130a in the perpendicular direction 152 becomes a length d. In this case, since the base material 121 has anisotropy with respect to expansion/contraction, the amount of stretch (c−a) of the elastic member 120 in the parallel direction 151 is smaller than that of an elastic member having isotropy. The amount of stretch (c−a) of the elastic member 120 in the parallel direction 151 may be smaller than the allowable margin of the intervals between the semiconductor substrates 130. In addition, the length b of the elastic member 120 in the perpendicular direction 152 may be larger than variations in the thicknesses of the semiconductor substrates 130.

The base material 121 may be formed by, for example, a polyolefin-based resin, polyester, unwoven fabric, chemical fiber, wire mesh, or the like. It is possible to use a polystyrene-based resin, of polyolefin-based resins, which has relatively high flexibility. This wire may be, for example, a metal wire or resin wire. It is possible to select, as a material for the adhesion layers 122 and 123, for example, at least one of the following materials: an acrylic material, epoxy-based material, rubber-based material, polyester-based material, polyamide-based material, vinyl alkylether-based material, and silicone-based adhesive material. In addition, it is possible to select, as a material for the adhesion layer 123, a combination of materials having heat-releasable adhesive layers including heat-expandable microspheres. This makes it possible to release the base material 121 from a plurality of semiconductor substrates 130 to replace, for example, some semiconductor substrates 130.

Figure 3:
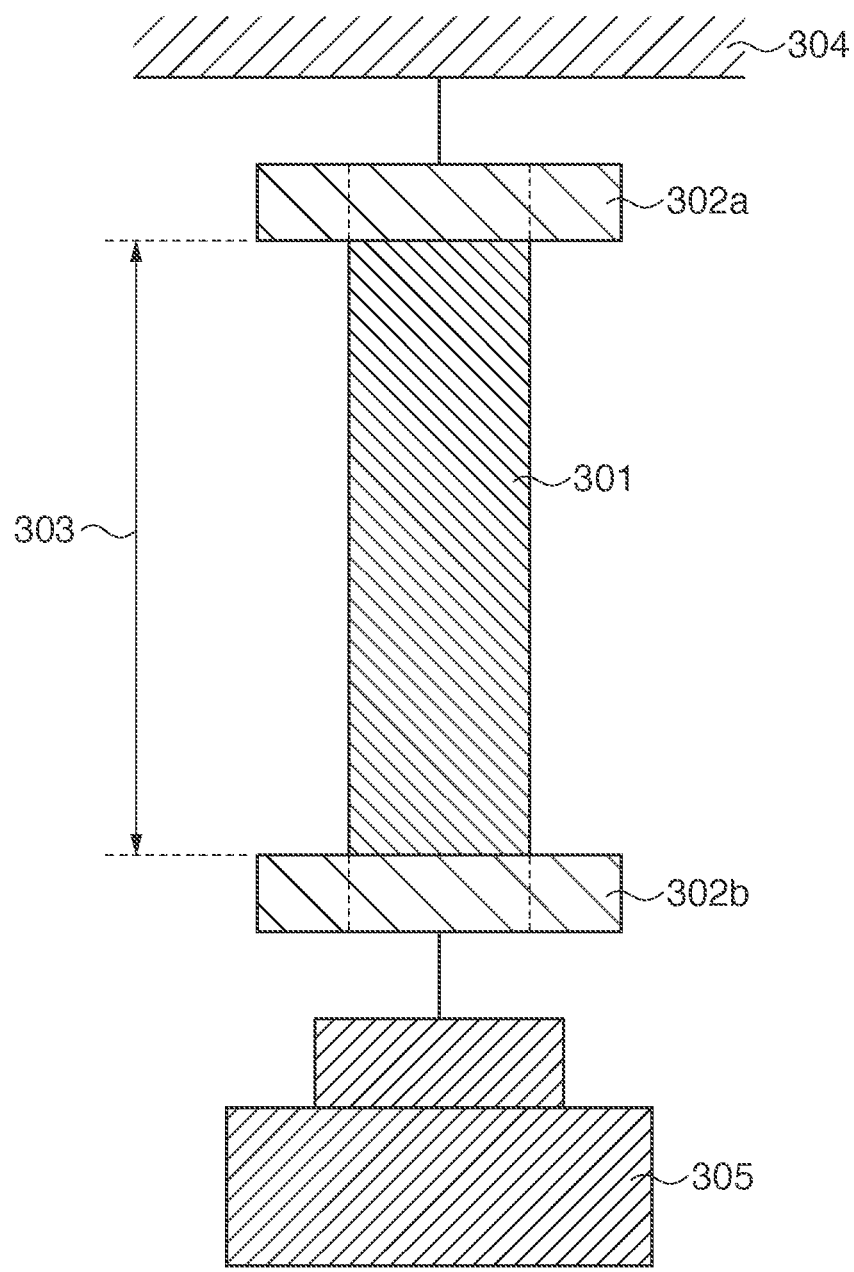
FIG. 3 is a view for explaining a method of measuring the amount of stretch of a base material.
Figure 4:
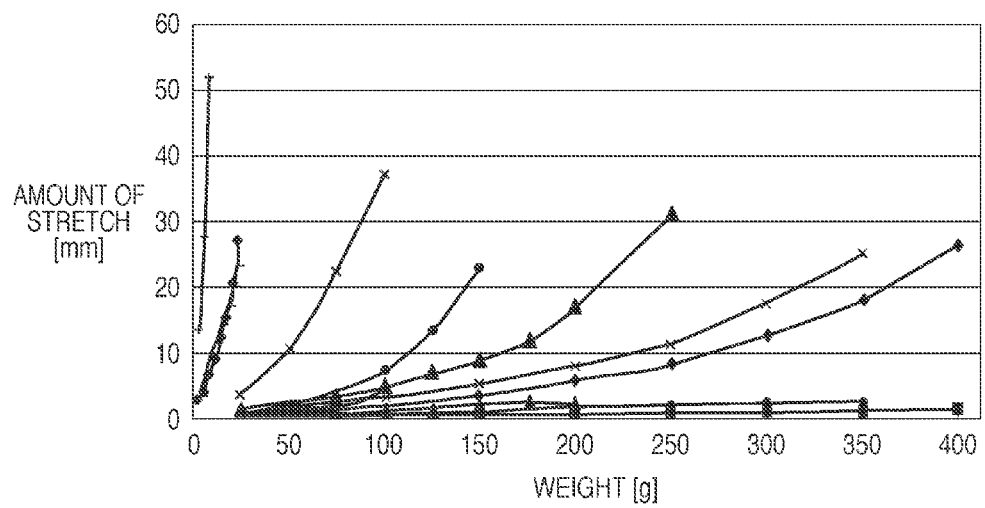
FIG. 4 is a graph for explaining the relationship between the amount of stretch of a base material and the weight of a weight member.

A method of measuring the amount of stretch of the base material 121 in the parallel direction 151 will be described next with reference to FIG. 3. The amount of stretch of the base material 121 in the parallel direction 151 when being compressed in the perpendicular direction 152 has a correlation with the amount of stretch of the base material 121 in the parallel direction 151 when being stretched in the parallel direction 151. In the following operation, therefore, the amount of stretch of a specimen when it is stretched is measured. The amount of stretch of the base material 121 in the perpendicular direction 152 can also be measured by the same measurement method. First of all, a specimen 301 is extracted from the base material 121 such that it has a length of 120 mm in the parallel direction 151 and a length of 10 mm in the perpendicular direction 152. Two PET (polyethylene terephthalate) sheets 302a and 302b each having a width of 20 mm and a length of 10 mm are prepared, and the weight of the PET sheet 302b is measured. The portions of the specimen 301, each having a length of 10 mm and extending from a corresponding end portion by 10 mm, are tucked into the PET sheets 302a and 302b, respectively. In this case, the center lines of the specimen 301 and PET sheets 302a and 302b coincide with each other. Tucking the specimen 301 into the PET sheets 302a and 302b in this manner makes the elastic portion of the specimen 301 have a length 303 of 100 mm. The PET sheet 302a is suspended from a support member 304. In this state, the length 303 is measured. The value obtained by subtracting 100 mm from the length 303 in the suspended state is equivalent to the amount of stretch of the specimen 301 due to the weight of the PET sheet 302b. Weight members 305 of various weights are then suspended from the PET sheet 302b, and the amounts of stretch of the specimen 301 are measured. With regard to the suspended weight member 305, the value obtained by subtracting 100 mm from the length 303 is equivalent to the amount of stretch of the specimen 301, which corresponds to the sum of the weights of the PET sheet 302b and weight member 305. FIG. 4 is a graph showing the relationship between the sums of the weights of specimens 301 made of various materials and the weights of weight members and the amounts of stretch. For example, letting d be the amount of stretch and x be the weight of the weight member 305, it is possible to select the base material 121 which satisfy d≤0.563exp (0.00253x) and use it for the radiation detection apparatus 100.

Figure 5:
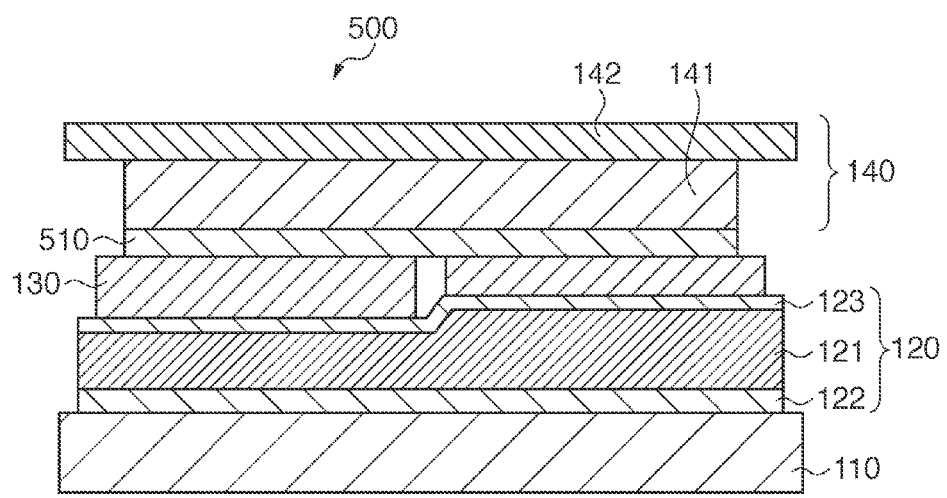
FIG. 5 is a schematic sectional view of another example of the radiation detection apparatus according to a second embodiment.

A modification of the above embodiment will be described below with reference to FIG. 5. The same reference numerals as in FIG. 1 denote the same constituent elements in FIG. 5, and a description of them will be omitted. A semiconductor detection apparatus 500 shown in FIG. 5 includes an adhesion layer 510 between the scintillator layer 141 and the semiconductor substrates 130. The scintillator layer 141 is bonded to the semiconductor substrates 130 through the adhesion layer 510.

As described above, according to the above embodiment, since the elastic member which supports the plurality of semiconductor substrates 130 has anisotropy with respect to expansion/contraction, it is possible to suppress shifts in the intervals between the respective semiconductor substrates.

The example of the above embodiment will be described below.

First Example

Assume that the first example uses, as a material for a base material 121, a PET material of the above materials which has relatively high hardness, with the thickness being 10 μm or more and 500 μm or less. The first example also selects, as a material for an adhesion layer 123, a material from materials having heat-releasable adhesive layers including heat-expandable microspheres. In addition, an adhesion layer 122 has a thickness of 10 μm or more and 100 μm or less. The first example uses a material having relatively high hardness for the base material 121 to suppress the expansion/contraction of the adhesion layer 123 in a parallel direction 151 when releasing semiconductor substrates 130 from the base material 121 by heating the adhesion layer 123. This prevents the semiconductor substrates 130 from colliding with each other.

Second Example

The second example associated with the modification described above with reference to FIG. 5 will be described below. Since semiconductor substrates 130 may have different thicknesses, bubbles may enter between an adhesion layer 510 and the semiconductor substrates 130 when a scintillator panel 140 is bonded to the semiconductor substrates 130. Even if vacuum/pressure defoaming processing is performed to remove the bubbles, some bubbles may remain. The presence of residual bubbles will degrade the quality of an output image because light which is converted by the scintillator panel 140 and propagates toward the semiconductor substrates 130 changes due to reflection and refraction.

The second example therefore uses, as a material for a base material 121, a PET material of the above materials which has relatively high hardness, and sets the thickness of the base material 121 to 10 μm or more and 50 μm or less. Although it is possible to use the above material as a material for an adhesion layer 123, it is possible to select a material from materials having heat-releasable adhesive layers including heat-expandable microspheres, in particular, to facilitate replacement of the semiconductor substrate 130. This makes it possible for an adhesion layer 122 and the adhesion layer 123 to efficiently absorb shifts of the semiconductor substrates 130 in a perpendicular direction 152. This prevents shifts of the semiconductor substrates 130 in a parallel direction 151 and residual bubbles between the semiconductor substrates 130 and the adhesion layer 510 after vacuum/pressure defoaming processing.

Third Example

The third example associated with the modification described with reference to FIG. 5 will be described below. The third example uses, as an adhesion layer 122, an elastic adhesive layer formed by an elastic adhesive material. In this case, the elastic adhesive layer may have anisotropy with respect to expansion/contraction like a base material 121. For example, a sheet-like polystyrene material is used as a material for the base material of the elastic adhesive layer, and a damper sheet using an acrylic adhesive material is especially effective as each of adhesive layers on the two surfaces of the base material. As a base material for the elastic adhesive layer, a polyolefin-based resin, polyester, or the like can be used. It is also possible to use a non-elastic material as the adhesion layer 122 instead of the above material, and to place an elastic adhesive layer (not shown) between the adhesion layer 122 and a base 110. This prevents shifts of semiconductor substrates 130 in a parallel direction 151 and residual bubbles between the semiconductor substrates 130 and an adhesion layer 510 after vacuum/pressure defoaming processing, even if PET is used as a material for the base material 121 and its thickness is 50 μm or more and 500 μm or less. The third example uses, as a material for an adhesion layer 123, the same material as that in each of the first and second examples, and can select a material from materials having heat-releasable adhesive layers including heat-expandable microspheres, in particular.

Other Embodiments

Figure 6:
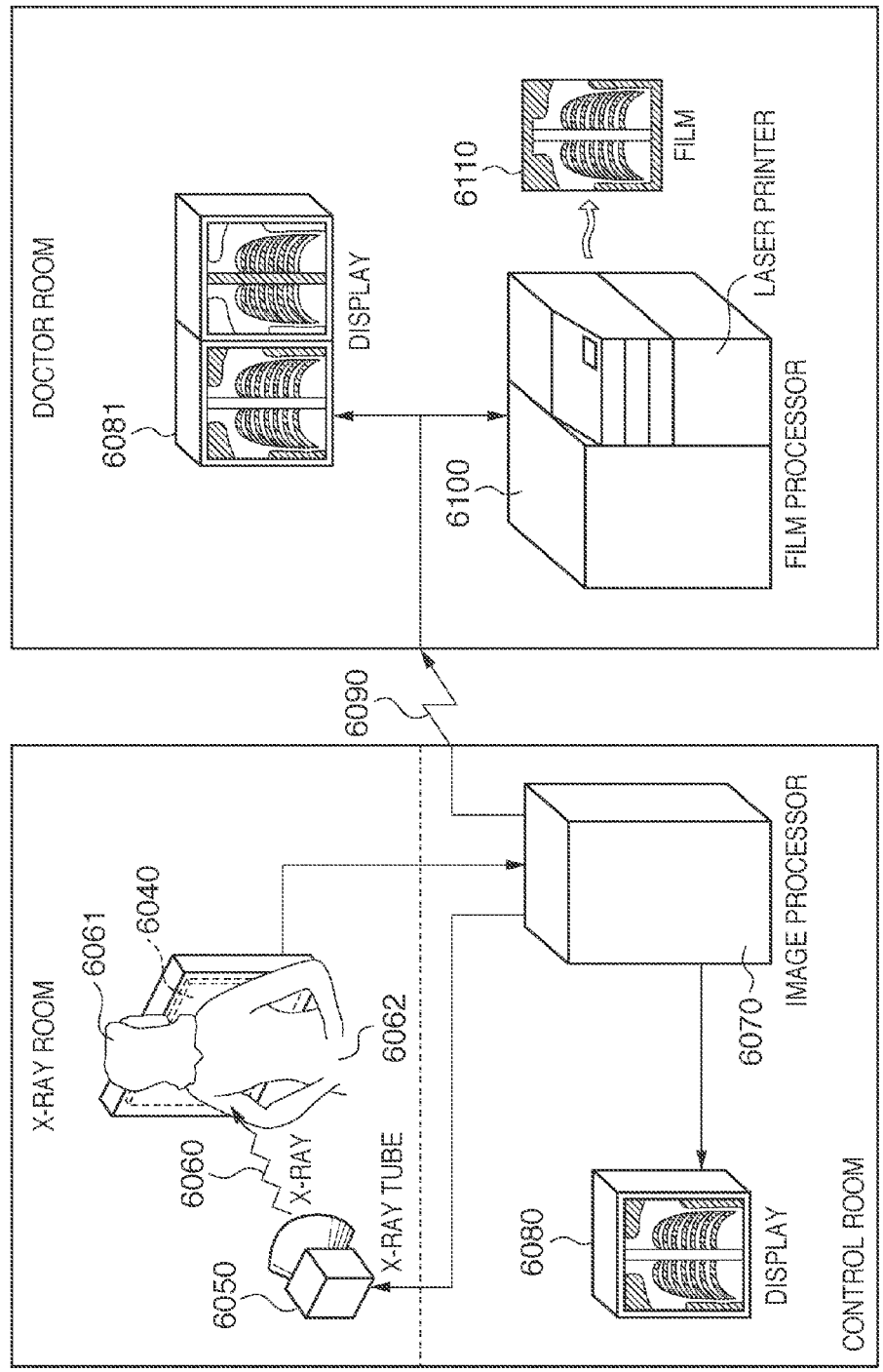
FIG. 6 is a view for explaining a radiation imaging system according to another embodiment.

FIG. 6 is a view showing an example of the application of an X-ray imaging apparatus according to the present invention to an X-ray diagnostic system (radiation imaging system). An X-ray 6060 generated by an X-ray tube 6050 (radiation source) is transmitted through a chest region 6062 of a patient 6061 and strikes a photoelectric conversion apparatus 6040 (a photoelectric conversion apparatus having a scintillator mounted on its upper portion forms the above radiation detection apparatus) having a scintillator mounted on its upper portion. The incident X-ray contains information inside the body of the patient 6061. The scintillator emits light when X-rays strike it. This light is photoelectrically converted to obtain electrical information. This information is converted into a digital signal. An image processor 6070 serving as a signal processing unit performs image processing for the digital signal to allow observation of the resultant image on a display 6080 serving as a display unit in a control room. Note that the radiation imaging system includes at least an imaging apparatus and a signal processing unit which processes signals from the imaging apparatus.

In addition, a transmission processing unit on a network 6090 such as a telephone line or the Internet can transfer this information to a remote place to allow the information to be displayed on a display 6081 serving as a display unit or be stored in a recording unit such as an optical disk in a doctor's room or the like in another place. This allows a doctor to perform diagnosis in a remote location. In addition, a film processor 6100 serving as a recording unit can record the information on a film 6110 serving as a recording medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-143919, filed Jun. 24, 2010, and No. 2010-255311, filed Nov. 15, 2010, which are hereby incorporated by reference herein in their entirety.

What is claimed is:

1. A radiation detection apparatus comprising:
 a plurality of semiconductor substrates each having a first surface on which a photoelectric conversion portion for detecting light is formed and a second surface opposite to said first surface;
 a scintillator layer, placed over said first surfaces of said plurality of semiconductor substrates, for converting radiation into light; and
 an elastic member, placed between a base and said second surfaces of the plurality of semiconductor substrates, for supporting said second surfaces of said plurality of semiconductor substrates such that said first surfaces of said plurality of semiconductor substrates are aligned flush with each other,
 wherein, in measurement of said elastic member as a single body, an amount of stretch of a cubic specimen in a direction parallel to said first surface when being compressed in a direction perpendicular to said first surface is smaller than an amount of stretch of the specimen in the direction perpendicular to said first surface when being compressed in the direction parallel to said first surface.

2. The apparatus according to claim 1, wherein said elastic member includes a base material formed by at least one of unwoven fabric, chemical fiber, and wire mesh.

3. The apparatus according to claim 2, wherein said elastic member further includes a heat-releasable adhesive layer for bonding said plurality of semiconductor substrates to said base material.

4. The apparatus according to claim 2, wherein said elastic member further includes an elastic adhesive layer for bonding said base material to the base.

5. A radiation imaging system comprising:
 a radiation detection apparatus according to claim 1; and
 a signal processing unit configured to process a signal obtained from said radiation detection apparatus.

6. The apparatus according to claim 1, wherein said plurality of semiconductor substrates have different thickness from each other.

7. The apparatus according to claim 1, wherein said second surfaces of said plurality of semiconductor substrates have different heights from the base from each other.

8. A radiation detection apparatus comprising:
a plurality of semiconductor substrates each having a first surface on which a photoelectric conversion portion for detecting light is formed and a second surface opposite to said first surface;
a scintillator layer, placed over said first surfaces of said plurality of semiconductor substrates, for converting radiation into light; and
an elastic member, placed over a base, for supporting said second surfaces of said plurality of semiconductor substrates such that said first surfaces of said plurality of semiconductor substrates are aligned flush with each other,
wherein an amount of stretch of said elastic member in a direction parallel to said first surface is smaller than an amount of stretch of said elastic member in a direction perpendicular to said first surface.

9. A radiation detection apparatus comprising:
a plurality of semiconductor substrates each having a first surface on which a photoelectric conversion portion for detecting light is formed and a second surface opposite to said first surface;
a scintillator layer, placed over said first surfaces of said plurality of semiconductor substrates, for converting radiation into light; and
an elastic member, placed over a base, for supporting said second surfaces of said plurality of semiconductor substrates such that said first surfaces of said plurality of semiconductor substrates are aligned flush with each other,
wherein a stretch rate of said elastic member in a direction parallel to said first surface is smaller than a stretch rate of said elastic member in a direction perpendicular to said first surface.

* * * * *